(12) United States Patent
Taylor

(10) Patent No.: US 8,734,722 B2
(45) Date of Patent: May 27, 2014

(54) DETECTION APPARATUS ACCOMPANYING PRECONCENTRATED PULSED ANALYTE VIA AN APERTURE

(75) Inventor: Stephen John Taylor, Hyde Heath (GB)

(73) Assignee: Smiths Detection-Watford Limited, Watford, Hertfordshire (GB)

( * ) Notice: Subject to any disclaimer, the term of this patent is extended or adjusted under 35 U.S.C. 154(b) by 812 days.

(21) Appl. No.: 12/521,542

(22) PCT Filed: Dec. 10, 2007

(86) PCT No.: PCT/GB2007/004711
§ 371 (c)(1),
(2), (4) Date: Jun. 26, 2009

(87) PCT Pub. No.: WO2008/074986
PCT Pub. Date: Jun. 26, 2008

(65) Prior Publication Data
US 2010/0317125 A1    Dec. 16, 2010

(30) Foreign Application Priority Data
Dec. 20, 2006 (GB) .................................. 0625478.3

(51) Int. Cl.
*G01N 1/40* (2006.01)
*G01N 33/00* (2006.01)

(52) U.S. Cl.
USPC .......................................... 422/83; 422/68.1

(58) Field of Classification Search
USPC .............. 250/287, 288, 281, 282, 397, 428, 250/441.11, 286; 422/83, 62, 67, 68.1, 89, 422/50, 69, 88; 436/43, 173, 174, 177, 178, 436/181
See application file for complete search history.

(56) References Cited

U.S. PATENT DOCUMENTS

| 3,107,966 A | 10/1963 | Bonhomme |
| 3,461,285 A | 8/1969 | Werner et al. |
| 3,470,527 A | 9/1969 | Bonhomme |
| 3,787,681 A | 1/1974 | Brunnee et al. |

(Continued)

FOREIGN PATENT DOCUMENTS

| EP | 0135747 | 4/1985 |
| GB | 2323165 | 9/1998 |

(Continued)

OTHER PUBLICATIONS

Creaser, Colin S. et al. "Ion mobility spectrometry: a review. Part 1. Structural analysis by mobility measurement." The Analyst (2004) 129 984-994.*

(Continued)

*Primary Examiner* — Christopher A Hixson
(74) *Attorney, Agent, or Firm* — Reinhart Boerner Van Deuren s.c.

(57) ABSTRACT

IMS apparatus has a preconcentrator outside its inlet aperture. Analyte vapor is adsorbed during a first phase when substantially no gas is admitted to the reaction region. The preconcentrator is then energized to desorb the analyte molecules and create a volume of desorbed molecules outside the IMS housing. Next, a pressure pulser is energized momentarily to drop pressure in the housing and draw in a small sip of the analyte molecules from the desorbed volume through the aperture. This is repeated until the concentration of analyte molecules in the desorbed volume is too low for accurate analysis, following which the apparatus enters another adsorption phase.

15 Claims, 1 Drawing Sheet

(56) References Cited

U.S. PATENT DOCUMENTS

| | | | |
|---|---|---|---|
| 4,378,499 A | 3/1983 | Spangler et al. |
| 4,551,624 A | 11/1985 | Spangler et al. |
| 5,083,019 A | 1/1992 | Spangler |
| 5,227,628 A | 7/1993 | Turner |
| 5,304,797 A | 4/1994 | Irie et al. |
| 5,574,277 A | 11/1996 | Taylor |
| 5,723,861 A | 3/1998 | Carnahan et al. |
| 5,854,431 A | 12/1998 | Linker et al. |
| 5,952,652 A | 9/1999 | Taylor et al. |
| 6,051,832 A | 4/2000 | Bradshaw |
| 6,073,498 A | 6/2000 | Taylor |
| 6,102,746 A | 8/2000 | Nania et al. |
| 6,225,623 B1 | 5/2001 | Turner et al. |
| 6,239,428 B1 | 5/2001 | Kunz |
| 6,442,997 B1 | 9/2002 | Megerle |
| 6,459,079 B1 | 10/2002 | Machlinski et al. |
| 6,481,263 B1 | 11/2002 | Haley |
| 6,495,824 B1 | 12/2002 | Atkinson |
| 6,502,470 B1 | 1/2003 | Taylor et al. |
| 6,523,393 B1 | 2/2003 | Linker et al. |
| 6,825,460 B2 | 11/2004 | Breach et al. |
| 7,098,449 B1 | 8/2006 | Miller et al. |
| 7,118,712 B1 | 10/2006 | Manginell |
| 7,311,566 B2 | 12/2007 | Dent |
| 2002/0150923 A1 | 10/2002 | Malik |
| 2004/0259265 A1 | 12/2004 | Bonne |
| 2005/0017163 A1 | 1/2005 | Miller et al. |
| 2005/0095722 A1 | 5/2005 | McGill et al. |
| 2005/0109931 A1* | 5/2005 | Schultz et al. ............... 250/287 |
| 2005/0109932 A1* | 5/2005 | Mullock et al. ............... 250/288 |
| 2005/0161596 A1 | 7/2005 | Guevremont et al. |
| 2005/0178975 A1 | 8/2005 | Glukhoy |
| 2005/0253061 A1 | 11/2005 | Cameron et al. |
| 2006/0249673 A1 | 11/2006 | Breach et al. |

FOREIGN PATENT DOCUMENTS

| | | |
|---|---|---|
| WO | WO 9301485 | 1/1993 |
| WO | WO 9322033 | 11/1993 |
| WO | WO 9921212 | 4/1999 |
| WO | WO 0079261 | 12/2000 |
| WO | WO 0195999 | 12/2001 |
| WO | WO 02078047 | 10/2002 |
| WO | WO 2004012231 | 2/2004 |
| WO | WO 2006046077 | 5/2006 |
| WO | WO 2008035095 | 3/2008 |

OTHER PUBLICATIONS

Ritter, Leah S. et al. "Solid phase micro-extraction in a miniature ion trap mass spectrometer." The Analyst (2003) 128 1119-1122.*

Jiao, Charles Q. et al. "A pulsed-leak valve for use with ion trapping mass spectrometers." J Am Soc Mass Spectrom (1996) 7 118-122.*

* cited by examiner

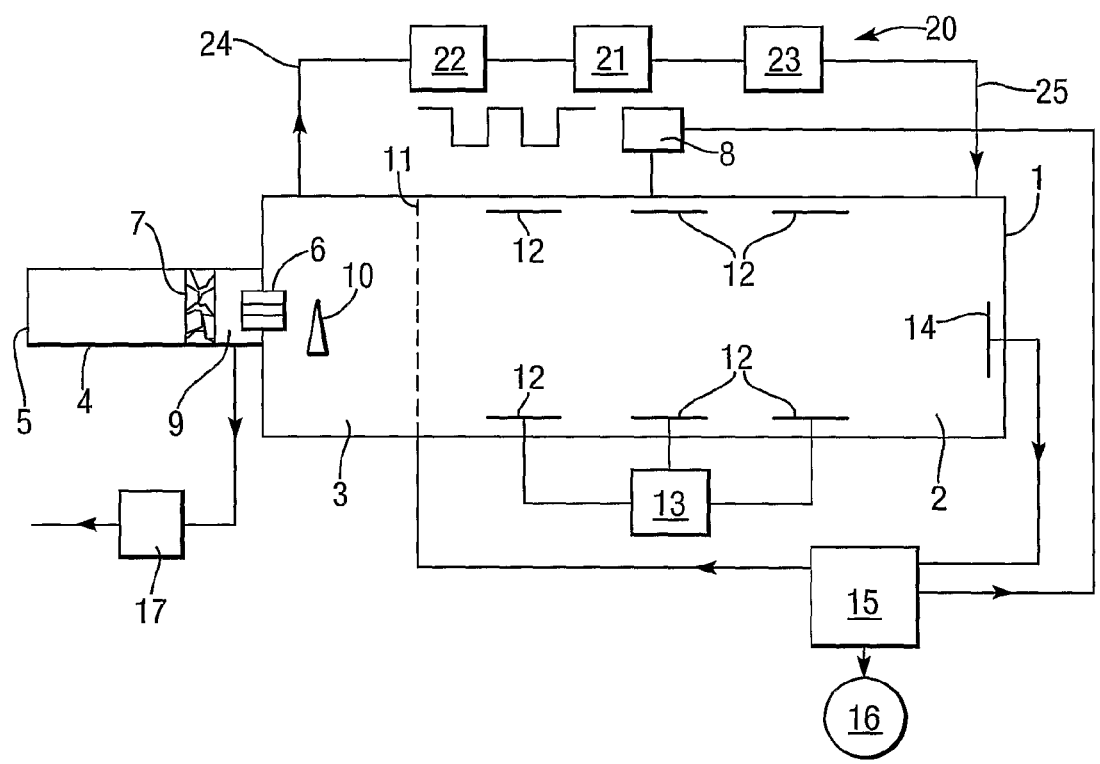

DETECTION APPARATUS ACCOMPANYING PRECONCENTRATED PULSED ANALYTE VIA AN APERTURE

This application is related to three other concurrently filed copending patent applications, namely U.S. patent application Ser. No. 12/521,537, entitled "Detection Apparatus," U.S. patent application Ser. No. 12/521,546, entitled "Detector Apparatus and Preconcentrators," and U.S. patent application Ser. No. 12/521,549, entitled "Gas Preconcentrator for Detection Apparatus," all assigned to the assignee of the present patent application, which three patent applications are hereby incorporated herein by reference.

BACKGROUND OF THE INVENTION

Field of the Invention

This invention relates to detection apparatus of the kind for detecting or analyzing an analyte sample gas or vapor, the apparatus having an aperture through which analyte sample gas or vapor is admitted.

Ion mobility spectrometers or IMS apparatus are often used to detect substances such as explosives, drugs, blister and nerve agents, or the like. An IMS apparatus typically includes a detector cell to which a sample of air containing a suspected substance or analyte is continuously supplied as a gas or vapor. The cell operates at or near atmospheric pressure and contains electrodes energized to produce a voltage gradient along the cell. Molecules in the sample of air are ionized, such as by means of a radioactive source, UV source, or by corona discharge, and are admitted into the drift region of the cell by an electrostatic gate at one end. The ionized molecules drift to the opposite end of the cell at a speed dependent on the mobility of the ions. By measuring the time of flight along the cell, it is possible to identify the ions. In conventional IMS apparatus clean dry gas flows continuously through the reaction or ionization region. This arrangement allows for continuous sampling and short recovery times. Where the sample analyte is only present in small concentrations in the sample gas, there can be a relatively low signal-to-noise ratio and this can make reliable detection very difficult.

It is accordingly desirable to provide alternative detection apparatus.

SUMMARY OF THE INVENTION

According to one aspect of the present invention there is provided a detection apparatus of the above-specified kind, characterized in that the detection apparatus is arranged to establish a volume of analyte outside the detection apparatus and to supply analyte from the volume into the detection apparatus via an aperture in bursts smaller than that of the volume separated by periods when no analyte gas or vapor is admitted.

The detection apparatus preferably includes a preconcentrator by which the volume of analyte outside the apparatus is established. The preconcentrator may include polydimethylsiloxane.

The detection apparatus preferably includes a pressure pulser connected with the interior of the detection apparatus by which the bursts of analyte are supplied into the detection apparatus. The detection apparatus may be an IMS, with the aperture opening into a reaction region and the reaction region opening into a drift region.

According to another aspect of the present invention there is provided a method of detecting an analyte sample gas or vapor, characterized in that the method includes the steps of establishing a volume of analyte, admitting bursts of analyte molecules less than the established volume to a reaction region, with the bursts being separated by periods of time during which substantially no analyte molecules are admitted, and detecting the presence of the admitted analyte molecules.

The volume of analyte is preferably established by adsorption and desorption. The analyte is preferably adsorbed while there is substantially no flow into the reaction region, with the analyte being subsequently desorbed and pressure momentarily reduced to draw desorbed analyte molecules into the reaction region. The pressure may be repeatedly reduced to draw a plurality of sips of analyte molecules from the desorbed molecules progressively to deplete the analyte molecules in the volume. Analyte sample gas or vapor may be adsorbed again by preconcentration, and pressure reduction may be stopped when the concentration of analyte in the volume has been depleted to an extent where analysis becomes less reliable, with desorption and pressure reduction being restarted again after sufficient time for detectable amounts of analyte to be released.

DESCRIPTION OF THE DRAWINGS

An IMS apparatus that is constructed and operated according to the present invention will now be described, by way of example, with reference to the accompanying FIG. 1, which shows IMS apparatus schematically.

DETAILED DESCRIPTION OF THE PREFERRED EMBODIMENT

With reference to FIG. 1, the detection apparatus takes the form of an ion mobility spectrometer ("IMS") having a generally tubular housing 1 with an analysis or drift region 2 towards its right-hand end (as shown in FIG. 1) and an ionization or reaction region 3 towards its opposite left-hand end (as shown in FIG. 1).

An inlet conduit 4 opens at one end 5 to air or another source of gas or vapor to be sampled and analyzed. At its other end, the inlet conduit 4 connects with a pump 17, by which the sample is drawn through the inlet conduit 4, and an aperture 6 provided by a capillary passage or pin-hole, which communicates between the inlet conduit 4 and the interior of the reaction region 3 so that molecules of interest can pass from the inlet conduit 4 into the reaction region 3. The aperture 6 could be provided by a membrane or other similar apparatus. The inlet conduit 4 includes a preconcentrator 7 or other similar apparatus for establishing a volume of analyte gas or vapor, the purpose of which will be described later.

The reaction region 3 contains apparatus to ionize molecules of the analyte substance, such as a corona discharge point 10, at a high potential. The reaction region 3 and the drift region 2 are both at atmospheric pressure or just slightly below atmospheric pressure. The reaction region 3 and the drift region 2 may be separated from one another by an optional, conventional electrostatic shutter 11 such as a Bradbury Nielson gate by which the flow of ions into the drift region 2 may be controlled. The drift region 2 has a series of pairs of electrodes 12 on opposite sides thereof which are longitudinally spaced from one another along the length of the drift region 2. A voltage supply 13 applies a voltage to each electrode pair 12, which voltage increases from the left to the right along the length of the drift region (as shown in FIG. 1) so that ions passed by the electrostatic shutter 11 are subject to a voltage gradient, which draws them along the length of the drift region 2. A collector plate 14 mounted at the far, right-hand end of the drift region 2 (as shown in FIG. 1) collects ions after passage along the drift region 2. The charge produced by each ion when it impacts the collector plate 14 is supplied as an electrical signal to a processor unit 15. The processor unit 15 analyzes the signals to produce spectra representative of the mobility of the different ions detected and supplies these to a display or other utilization apparatus 16.

A gas flow system 20 provides a flow of clean dry air along the inside of the housing 1 against the flow of the ions. The gas flow system includes a pump 21 with molecular sieve inlet and outlet filters 22 and 23 respectively located at its inlet and outlet. The inlet filter 22 connects with an inlet pipe 24, which opens into the housing 1 towards the inlet end of the reaction region 3 (shown on the left end in FIG. 1). The outlet filter 23 connects with an outlet pipe 25, which opens into the housing 1 towards the downstream end of the drift region 2 (shown on the right end in FIG. 1). The pump 21 operates to draw gas from the reaction region 3 so that it flows through the first filter 22, the pump 21, and the second filter 23 before flowing back into the housing 1 at the right-most end of the drift region 2 (as shown in FIG. 1).

The apparatus also includes a pressure pulser 8, which may be an electromagnetic transducer similar to a loudspeaker, which is connected to the housing 1 in the manner described in U.S. Pat. No. 6,073,498, to Taylor et al., which is hereby incorporated herein by reference. The pressure pulser is operated intermittently, momentarily to draw small volumes of sample vapor or gas into the reaction region 3 to produce a pressure pulse pattern of the kind illustrated.

The preconcentrator 7 includes a quantity of a material that will adsorb analyte vapor of interest and that can be arranged to desorb the vapor. A typical material that could be used is polydimethylsiloxane. Baffles could be arranged around the preconcentrator 7 to reduce sample losses due to diffusion. The preconcentrator 7 is located close to the aperture 6.

In operation, during the adsorption phase, air to be sampled is flowed into the conduit 4 by means of the pump 17 so that there is a continuous flow in and out of the conduit 4. During this adsorption phase, analyte vapor is adsorbed by the preconcentrator 7 and there is substantially no flow into the housing 1. The apparatus then goes through a desorption phase during which the pump 17 is turned off so that the inlet flow to the conduit 4 is stopped to prevent the collected sample from being blown away. The preconcentrator 7 is then heated or otherwise actuated to release the adsorbed analyte vapor into the volume 9 between the preconcentrator 7 and the aperture 6. At the same time, the pump 21 is turned off, or flow is substantially reduced, to prevent or reduce gas flow along the housing 1. The pressure pulser 8 is then activated to cause pulsed reductions in pressure within the housing 1. This has the effect of drawing in small bursts, puffs, or sips of the vapor in the volume 9 through the aperture 6 as jets into the reaction region 3. The vapor in each such burst is ionized in the reaction region 3, and ion mobility spectra are produced by the processor unit 15. The volume of each burst caused by the pressure pulser 8 is substantially less than the static volume of vapor established by the preconcentrator 7 in the volume 9. As such, the pressure pulser 8 can take many sips of the static vapor in the volume 9 before the concentration of the analyte in the volume 9 becomes depleted to an extent that the spectra produced become unreliable. When this happens, the detector reverts again to an adsorption phase.

By taking multiple sips from an established volume of analyte vapor, many spectra samples can be obtained, thereby enabling prolonged averaging and an increase in the signal-to-noise ratio. This is especially valuable where the analyte is only present in very low concentrations. The small sips of sample taken also avoid overloading the detector with excessive quantities of analyte substance where it is present in high quantities and enable the dynamic range of the detector apparatus to be extended. If the vapor concentration detected in the first burst is high, the detector apparatus could be arranged such that no further bursts are taken. Furthermore, the arrangement of the present invention avoids the problems that can occur when a high level of moisture is present, since this can prevent efficient ionization. By taking small bursts, the moisture is diluted to an extent such that it does not prevent detection of the compounds of interest.

Although it is preferable for gas flow within the housing 1 that are produced by the gas flow system 20 to be stopped when sample bursts are drawn into the reaction region 3, it is not essential to do so, since the flow could be maintained to flush away the sample burst, providing that the sample stays within the reaction region 3 sufficiently long for analysis to take place. It should also be noted that it is not necessary to stop gas flow along the entire housing 1, since the detection apparatus could have a separate gas flow path within the reaction region 3. In such an arrangement, this separate gas flow could be stopped, and the remaining flow along the drift region 2 could be maintained. In another arrangement, the gas flow could be stopped when each burst is taken, and then restarted between bursts to flush away the analyte substance. Alternatively, the flow of gas through the reaction region 3 could be stopped for a period extending over several discrete bursts.

There are various alternative ways in which a volume of sample substance could be established. Microelectromechanical systems ("MEMS") processes can be used to construct small chambers containing sorbent material onto which the vapor is adsorbed and from which it is desorbed. Instead of using heat to desorb the adsorbed substance, it would be possible to use radiation, pressure, or vibration to encourage desorption, either by itself or in conjunction with some other process.

The present invention can be used to enable small concentrations of analyte to be detected with improved signal-to-noise ratio. The present invention is particularly useful in IMS apparatus, but may also have application in different forms of detectors.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A detection apparatus for detecting or analyzing an analyte sample gas or vapor, comprising:
   an aperture by which analyte sample gas or vapor is admitted to the detection apparatus; and
   a pressure pulser connected with the interior of the detection apparatus;
   wherein the detection apparatus is arranged and configured to establish a volume of analyte outside the aperture, and wherein the pressure pulser is energized momentarily to drop pressure in the detection apparatus to draw analyte from the volume into the detection apparatus via the aperture in bursts smaller than that of the volume separated by periods when the pressure pulser is not energized during which periods no analyte gas or vapor is admitted.

2. The detection apparatus defined in claim 1, additionally comprising:
   a preconcentrator by which the volume of analyte outside the aperture is established.

3. The detection apparatus defined in claim 2, wherein the preconcentrator comprises polydimethylsiloxane.

4. The detection apparatus defined in claim 1, wherein the detection apparatus comprises an ion mobility spectrometer, wherein the aperture opens into a reaction region, and wherein the reaction region opens into a drift region.

5. A detection apparatus comprising:
   a detection apparatus housing having a first end at which an analyte will be admitted to the detection apparatus housing and a second end opposite the first end;
   a pressure pulser connected with the interior of the detection apparatus housing which may be energized momentarily to drop pressure in the interior of the detection apparatus housing;
   a reaction region located in the detection apparatus housing adjacent the first end thereof;
   a drift region located in the detection apparatus housing between the reaction region and the second end of the detection apparatus housing;
   an inlet conduit having a first end to which an analyte may be supplied and a second end;
   a volume of analyte established in said inlet conduit adjacent the second end thereof; and
   an aperture via which an analyte sample is admitted from the second end of the inlet conduit into the reaction region in the detection apparatus housing in bursts smaller than that of the volume whenever the pressure pulser is energized momentarily to drop pressure in the detection apparatus separated by periods when the pressure pulser is not energized during which periods no analyte is admitted into the reaction region in the detection apparatus housing.

6. The detection apparatus defined in claim 5, additionally comprising:
   a preconcentrator located in the inlet conduit, the volume of analyte outside the aperture being established intermediate the preconcentrator and the second end of the inlet conduit.

7. The detection apparatus defined in claim 6, wherein the preconcentrator includes a material comprising: polydimethylsiloxane.

8. The detection apparatus defined in claim 5 wherein the pressure pulser is configured to repeatedly reduce pressure in the detection apparatus housing to draw a plurality of sips of analyte sample in the volume.

9. The detection apparatus defined in claim 5, wherein the inlet conduit comprises:
   a material that adsorbs the analyte during the periods of time during which substantially no analyte molecules are admitted to the reaction region and desorbs the analyte during the periods of time when analyte samples are admitted to the reaction region in bursts.

10. The detection apparatus defined in claim 5, additionally comprising:
    an ionizing apparatus located in the reaction region that ionizes molecules of the analyte gas or vapor that has been admitted to the reaction region.

11. The detection apparatus defined in claim 5, additionally comprising:
    an electrostatic shutter that controls the flow of ions from the reaction region to the drift region.

12. The detection apparatus defined in claim 5, additionally comprising:
    a plurality of longitudinally spaced-apart electrode pairs located in the drift region that establish an electrical field in the drift region which draws ions located in the drift region in a direction from the first end of the detection apparatus housing to the second end of the detection apparatus housing.

13. The detection apparatus defined in claim 5, additionally comprising:
    a collector plate located near the second end of the detection apparatus housing, the collector plate collecting ions passing to the second end of the detection apparatus housing and providing an output to a processor indicative of the ions detected by the collector plate.

14. The detection apparatus defined in claim 5, wherein the passage of analyte from the volume into the detection apparatus is controlled solely by the operation of the pressure pulser.

15. The detection apparatus defined in claim 1, wherein the passage of analyte from the volume into the detection apparatus is controlled solely by the operation of the pressure pulser.

* * * * *